US009526514B2

(12) United States Patent
Kelley et al.

(10) Patent No.: US 9,526,514 B2
(45) Date of Patent: Dec. 27, 2016

(54) PATIENT-SPECIFIC ASSEMBLIES, JIGS, AND METHODS FOR A PERSONALIZED TOTAL HIP ARTHROPLASTY SYSTEM

(71) Applicants: Todd Kelley, Cincinnati, OH (US); Vasile Nistor, Cincinnati, OH (US); Earnest Christopher Casstevens, Austin, TX (US); Justin Miller, Cincinnati, OH (US); Jacob James Stegman, Cincinnati, OH (US)

(72) Inventors: Todd Kelley, Cincinnati, OH (US); Vasile Nistor, Cincinnati, OH (US); Earnest Christopher Casstevens, Austin, TX (US); Justin Miller, Cincinnati, OH (US); Jacob James Stegman, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 320 days.

(21) Appl. No.: 14/208,166

(22) Filed: Mar. 13, 2014

(65) Prior Publication Data
US 2014/0276867 A1    Sep. 18, 2014

Related U.S. Application Data

(60) Provisional application No. 61/778,749, filed on Mar. 13, 2013.

(51) Int. Cl.
| | | |
|---|---|---|
| *A61B 17/17* | (2006.01) | |
| *A61F 2/46* | (2006.01) | |
| *A61B 17/15* | (2006.01) | |
| *A61B 17/56* | (2006.01) | |
| *A61F 2/34* | (2006.01) | |

(52) U.S. Cl.
CPC .......... *A61B 17/1746* (2013.01); *A61B 17/15* (2013.01); *A61B 17/175* (2013.01); *A61F 2/4609* (2013.01); *A61B 2017/568* (2013.01); *A61F 2002/3401* (2013.01); *A61F 2002/4687* (2013.01); *Y10T 29/49826* (2015.01)

(58) Field of Classification Search
CPC .......................... A61B 17/1746; A61B 17/175
See application file for complete search history.

(56) References Cited

U.S. PATENT DOCUMENTS

| | | | |
|---|---|---|---|
| 2005/0059978 A1 | 3/2005 | Sherry et al. | |
| 2005/0234461 A1 | 10/2005 | Burdulis, Jr. et al. | |
| 2010/0082035 A1 | 4/2010 | Keefer | |
| 2011/0190775 A1 | 8/2011 | Ure | |
| 2012/0123423 A1* | 5/2012 | Fryman ................. | A61B 17/15 606/89 |
| 2012/0265208 A1 | 10/2012 | Smith | |

* cited by examiner

*Primary Examiner* — Andrew Yang
(74) *Attorney, Agent, or Firm* — Dinsmore & Shohl LLP

(57) ABSTRACT

A patient-specific total hip arthroplasty system including surgical guide and jig instrumentation modeled by computer aided design using image data derived from a specific patient's relevant anatomy. Patient-specific jigs fit surface topography of portions of the acetabulum and femur of the patient and are designed to guide surgical implantation at very precise geometries unique to each patient. Patient-specific pin-locating jigs, pin-rail and spacer systems, acetabular reaming and impacting jigs, and femoral resection and version jigs are fabricated pre-operatively according to the models. Methods for fabricating jig components of the system and methods of performing a total hip arthroplasty utilizing the system are also disclosed.

33 Claims, 15 Drawing Sheets

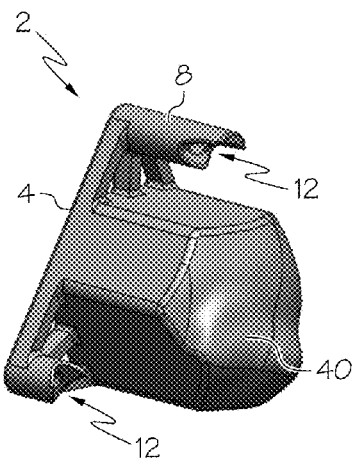
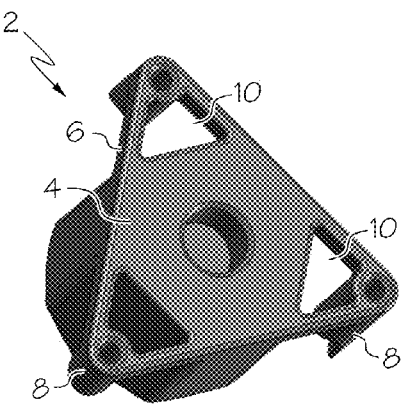
FIG. 3A  FIG. 3B
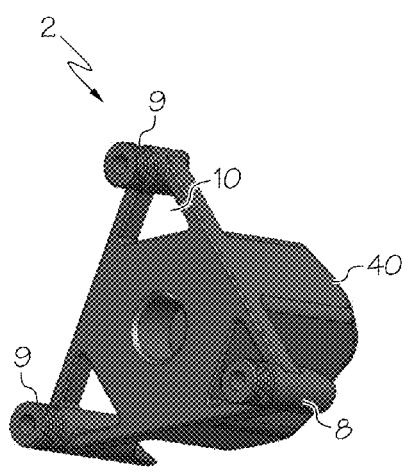
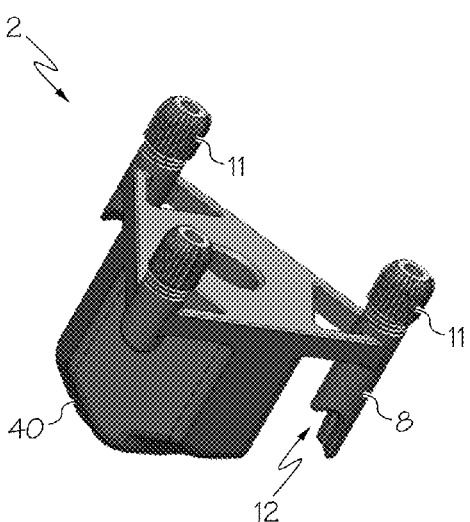
FIG. 3C  FIG. 3D

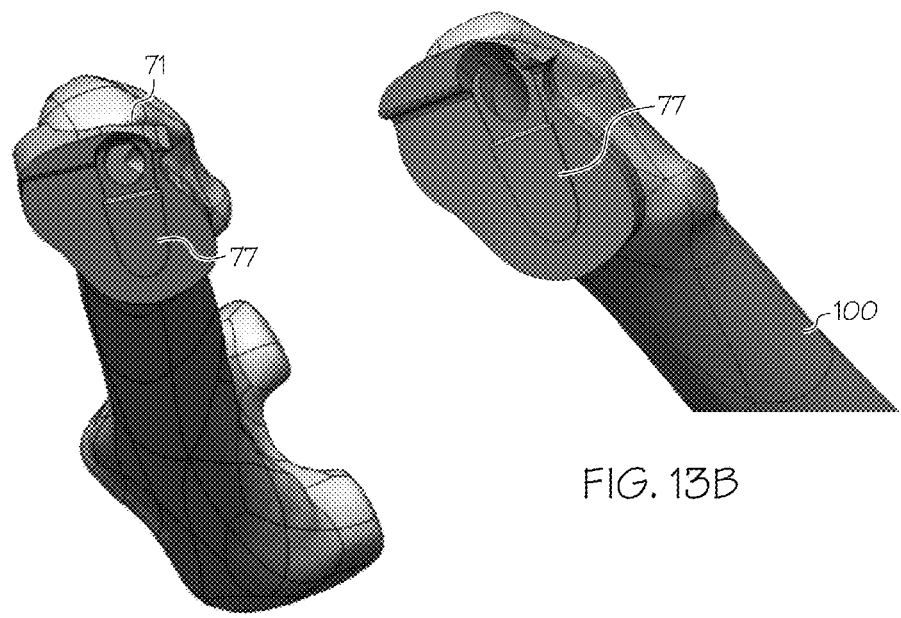
FIG. 13A
FIG. 13B
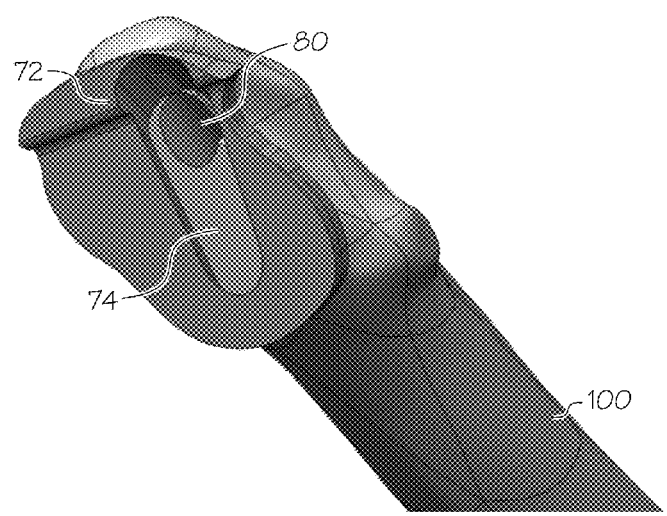
FIG. 13C

PATIENT-SPECIFIC ASSEMBLIES, JIGS, AND METHODS FOR A PERSONALIZED TOTAL HIP ARTHROPLASTY SYSTEM

CROSS REFERENCE TO RELATED APPLICATION

This application claims the benefit of U.S. Provisional Application No. 61/778,749 filed on Mar. 13, 2013, the entire disclosure of which is incorporated herein by this reference.

TECHNOLOGICAL FIELD

The present invention relates to a personalized total hip arthroplasty system. More particularly, the invention relates to patient-specific acetabular reaming and impacting jigs, and femoral resection and version jigs fabricated pre-operatively according to models generated via computer-assisted design based on imaging data derived from a specific patient.

BACKGROUND

In 2010, it was reported that one in four individuals will develop hip degenerative osteoarthritis in their lifetime. Total hip arthroplasty (THA) is becoming an increasingly common treatment for hip osteoarthritis with an estimated 12.6 replacements per 1000 individuals over the age of 18 in the United States from 2008-2009. THA has been successful in reducing and/or eliminating the pain associated with hip osteoarthritis because the previous end stage arthritis has been eliminated. However, there are still pitfalls associated with the THA procedure. Improper placement and alignment of the acetabular implant cup caused by misaligned reaming results in higher failure rates. In addition, the femoral stem must be implanted at a precise depth and angle, and with an appropriate neck length to maintain normal kinematics.

During THA, a surgical reamer is used to clear articular cartilage, tissue, and bone from the acetabulum to create an implantation site for the acetabular cup implant. The location and angle at which the reaming is done determines the final location and angulation of the implant. There is a specific angulation tolerance zone in which the implant should be located in order to minimize the chances of dislocation and need for revision surgery. Currently, there is not an adequate way of precisely determining the proper angulation intra-operatively. Generally, the surgeon estimates the angulation based off of pre-operative templating and intra-operative x-rays. The surgeon must also estimate angulation in this way when impacting the implant into the cup. It has been shown that when the acetabular component is implanted outside a specific "safe zone" of anteversion and vertical tilt, dislocation is 4 times more likely. It has also been shown that anteversion of the acetabular cup cannot be accurately assessed during surgery by orthopedic surgeons experienced in the THA procedure (Hassan D M, Johnston G H, Dut W N, Watson G, Dolovich A T. (1998) "Accuracy of intraoperative assessment of acetabular prosthesis placement." *The Journal of Arthroplasty.* 13(1), 80-84). It is also known that THA surgeons cannot consistently implant the acetabular cup within this "safe zone" (Digioia A M $3^{rd}$, Jaramaz B, Plakseychuk A Y, Moody J E Jr, Nikou C, Labarca R S, Levison T J, Picard F. (2002) "Comparison of a mechanical acetabular alignment guide with computer placement of the socket." *The Journal of Arthroplasty.* 17(3), 359-364). It is well-known that acetabular misalignment contributes to the risk of dislocation, incorrect leg length, impingement, pelvic osteolysis, acetabular migration, component wear, and a potential need for revision surgery.

During THA, a cut is made across the neck of the femur in order to remove the femoral head. The location of this cut plays a role in determining the resultant leg length of the patient. Currently, there is not an adequate way of precisely locating the correct cut line. The surgeon estimates where the cut should be made based off pre-operative templating. This often results in leg lengthening or shortening because of an incorrect cut location. When the femoral component is implanted too shallow or too deep, this results in the patient's limb being too long or too short, interrupting the patient's normal gait. Also, when the femoral implant is inserted into the canal, the appropriate angular orientation is not apparent because there is no indication of proper alignment. When the femoral component is implanted with too great of anteversion or retroversion, the frequency of dislocation is increased. This dislocation is due to the impingement of the femoral neck on the acetabular component.

Although computer-assisted design has been applied with some success to procedures for repair of articular surfaces, in particular of the knee, total hip arthroplasty is a much more challenging procedure involving integration of data from several anatomical planes and axes relating to implantation of prosthetics into disengaged ball-in-socket joint structures and then re-approximation of the implanted joint parts to form an integrated operational ball-in-socket joint with precise implant geometry. To the best of the knowledge of the present investigators, pre-operative imaging and CAD has not been applied to achieve a complete operational patient-specific THA system.

There remains a clear need in the art to improve the implant precision and patient-specificity of THA procedures.

SUMMARY

Accordingly, embodiments of the present invention utilize state of the art computer-aided design and three-dimensional modeling to create assemblies and systems of patient-specific jigs to guide surgical procedures and implantation of prosthetic devices in total hip arthroplasty. Pre-operative imaging of the femoral-acetabular region of the patient is used to create a three-dimensional construct of the surface topography of the patient's relevant bone structures, and a coordinate system based on anatomical reference points is created and superimposed on the constructs. Jigs are then created via three-dimensional modeling technology to provide the surgeon with indications of proper depth, angle, and version based on the patient's own physiology. Where the jigs position to the patient's bone, they are contoured to fit the precise surface topography of the patient's bone surface. The surgeon pre-operatively selects the site and position of an implant, and the jigs are modeled to achieve the surgeon's operational goals. Since the jigs are contoured to self-select a desired position on the bone, the amount of intra-operative discretion is reduced and intra-operative certainty is increased.

One embodiment of the invention provides a patient-specific acetabular reaming and impacting assembly. The assembly comprises a pin locating jig comprising a body having a periphery and a least three patient-specific cannulated nubs, each nub attached to the periphery by at least one tab and having at least one surface contoured to engage a portion of an outer rim of an acetabulum of the patient at a self-selecting position and through which a surgical pin may be inserted and secured to the outer rim of the acetabulum, where upon removal of the body a pin rail system is formed comprising at least three surgical pins, each secured through a nub forming a base; a removable reamer jig comprising at least three peripheral pin holes, each hole corresponding to a pin of the pin rail system permitting engagement of the reamer jig to the pin rail system, and an axial bore through which an acetabular reaming device may be inserted and attached; at least one set of spacing elements; a removable impactor jig comprising at least three peripheral pin holes, each hole corresponding to a pin of the pin rail system permitting sliding engagement of the impactor jig to the pin rail system, and a cup portion sized to fit into an implant cup, and an axial bore through which an acetabular impacting device may be inserted to guide and impact the implant into position in the acetabulum.

According to another embodiment, a patient-specific femoral resection jig is provided. The femoral resection jig comprises: a monolithic body having at least proximal, distal, medial and lateral surfaces, the distal surface providing a resection reference for guiding a cutting instrument to resect a femoral head, the medial surface comprising a patient-specific surface contoured as a negative to a surface of the patient's femoral neck such that the jig self-selects to engage a position on the surface of the femoral neck, and a medial-distal corner positioned upon engagement to provide a visual indicator of version.

An embodiment providing a patient-specific femoral version assembly is also provided. The femoral version assembly comprises a version guide contoured to fit a portion of a rim of a resected face of a femur and to substantially cover the resected face, the guide comprising an opening to the resected face into which a set of jig inserts including a standard reaming jig, a broaching jig and an implant placement jig may be seated and removed under operational conditions.

Methods for fabricating embodiments of patient-specific acetabular reaming and impacting assemblies, patient-specific femoral resection jigs, and patient-specific femoral version assemblies according to the disclosure are also provided.

Various embodiments and aspects of the inventive assemblies and jigs may be integrated into a total hip arthroplasty system which provides patient-specific control of hip geometry such that a femoral stem implant and an acetabular cup implant are positioned relative to one another with a hip geometry ideal for a specific patient.

These and other embodiments of the invention will be understood more clearly by reference to the figures and Detailed Description. Although figures may be described with precision, it is understood that the figures illustrate specific embodiments and that other configurations and designs are possible and within contemplation of the disclosure such that the figures should not be construed as limiting the full scope of the instant invention as defined by the claims.

BRIEF DESCRIPTION OF THE FIGURES

While the specification concludes with claims that particularly point out and distinctly claim embodiments of the invention, it is believed the present invention will be better understood from the following description of certain examples taken in conjunction with the accompanying figures. In the figures, like numerals represent like elements throughout the several views, and various components of the figures are not necessarily illustrated to scale.

FIG. 3A is an exterior bottom-facing view of an exemplary pin locating jig showing two contoured nub ends and a patient-specific contoured body surface; 3B is an exterior bottom view of the same jig showing three contoured nub ends and a patient-specific contoured body surface; 3C is a perspective view of an exemplary pin locating jig with threaded nubs; 3D illustrates the use of cannulated screw caps as spacer elements according to specific embodiments.

FIG. 13A depicts an exemplary patient-specific femoral version guide positioned on a resected femoral face and having a reaming jig inserted; 13B is another angle of the femoral version guide of A; 13C depicts the exemplary femoral version guide with the insert jig removed exposing a surface of the femoral face.

The figures are not intended to be limiting in any way, and it is contemplated that various embodiments of the invention may be carried out in a variety of other ways, including those not necessarily depicted in the figures. The accompanying figures incorporated in and forming a part of the specification illustrate several aspects of the present invention, and together with the description serve to explain the principles of the invention, it being understood, however, that this invention is not limited to the precise arrangements shown.

DETAILED DESCRIPTION

The present disclosure provides a personalized Total Hip Arthroplasty system. The following acronyms are used throughout the disclosure: THA—Total Hip Arthroplasty; CAD—Computer Aided Design; CT—Computed Tomography. The following definitions also apply. Acetabular vertical tilt is the angle from the sagittal plane on the coronal plane on the hip. Acetabular anteversion is the planar angle from the anterior perpendicular of the line of acetabular vertical tilt. Femoral anteversion is the angle from the coronal plane on the axial plane on the femur. A surgical reamer is a device used with a surgical drill to create an appropriately sized cavity in the acetabulum for implantation of an acetabular cup as a part of THA. A surgical impactor is a device used to impact the acetabular cup component into the acetabular cavity following reaming. A broach is a device used to create an appropriately sized cavity in the intramedullary canal of the femur for implantation of the femoral stem prosthetic component into the femur. A "trial" is a surgical device which replicates the implant and is placed in the joint prior to implantation to assist in finalizing an appropriate implant size. A jig is a tool or procedure-guiding device that may removably adhere to a structure and guide the tools and/or the surgeon operating on the structure. In some embodiments, a jig may be designed to operationally interact with another jig to ultimately guide tools and/or a surgeon operating on a structure. A jig is not generally a part of a prosthetic, but is intended to be removed from the surgical field after functional use. All terms not expressly defined herein are to be accorded their ordinary meaning in the arthroplastic arts.

Figure 1:
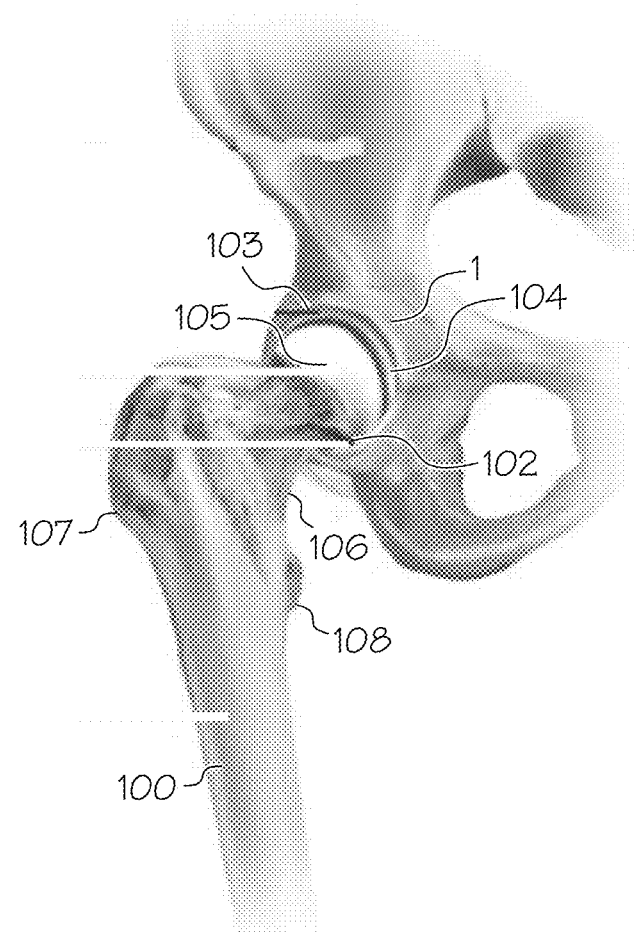
FIG. 1 illustrates the basic anatomical structure of the femoral-acetabular region.

Various illustrative embodiments and aspects of the inventive total hip arthroplasty (THA) system with jigs and jig-device assemblies will be discussed with reference to the accompanying Figures. The hip is a ball and socket joint. It is ordinarily very mobile with a large degree of motion. The two main components of the joint are the head 105 of the femur 100 and the acetabulum 1 as depicted in FIG. 1. There is articular cartilage 103 between the head 105 of the femur 100 and the acetabular cavity 102. The acetabular cavity 102 and the surrounding rim 104 comprise the acetabulum 1. The femoral neck 106 connects the femoral head 105 and a portion of the femur comprising the greater trochanter 107 and the lesser trochanter 108. The skeletal components are surrounded by musculature and connective tissue. During a THA it is important to do as little damage as possible to the surrounding musculature.

Generally, a THA procedure is fairly standard and includes the following procedural steps:

1. Gain access to the hip through an incision
2. Remove the capsule and dislocate the femoral head from the acetabular cup
3. Cut off the femoral head
4. Place prosthetic into femur
5. Ream acetabular cup
6. Place acetabular prosthetic into acetabular cup
7. Relocate the joint
8. Close incision Each step may include several distinct surgical procedures as well. It is well-known in the art to use temporary/removable jigs to guide placement of THA prosthetics. Known jigs may come in a variety of sizes, each intended to accommodate a range of patient sizes and geometries. Typically pre-operative imaging is employed to aid in determination of prosthesis and jig sizes; although a surgical team may keep several sizes available for rapid interchanging during a procedure where necessary. This rudimentary level of individualization of jigs is outside the scope of what is considered "patient specific" in accordance with the instant disclosure. "Patient-specific"

In accordance with some embodiments of the invention, a patient's hip is imaged, for example by CT-scanning and a CAD system is employed for pre-operative modeling of relevant jigs, including a patient-specific acetebular reaming and impacting jig system, and/or a femoral resection and femoral version jig. Although THA generally includes both aspects, one or the other of the procedures may be performed on any given patient as indicated by the patient's condition. For purposes of comprehensiveness, jig modeling/manufacture and implantation is discussed herein for a bilateral total hip replacement procedure.

Following the THA procedure, the patient's hip is again CT-scanned and the precision of the implantations may be evaluated. The use of the instantly inventive femoral resection jig in THA enhances precision and accuracy in location of a femoral neck resection, and permits refined anteversion of the femoral implantation. Accuracy in controlling the vertical tilt and anteversion of acetabulum implantation, and accuracy in controlling depth of acetabular implantation are enhanced by employing patient-specific manufacturing of jigs according to embodiments of the invention, wherein the jigs are manufactured according to models generated from CAD based on data derived from imaging a patient's unique anatomical features. The examples further illustrate the feasibility of performing a THA procedure with the inventive bone contouring resection, reaming, and impaction devices.

Figure 4A:
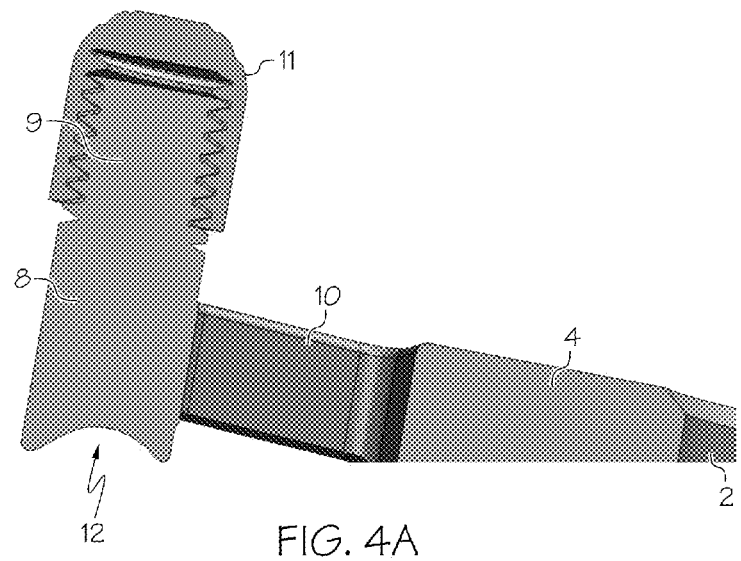
FIG. 4A is a sagittal cross-sectional view of a nub of a pin-locating jig with a spacer element comprising a cannulated screw cap engaged to the threaded end of the nub; 4B shows a specific embodiment of a pin-locating jig prior positioned in the acetabulum prior to insertion of surgical pins.
Figure 4B:
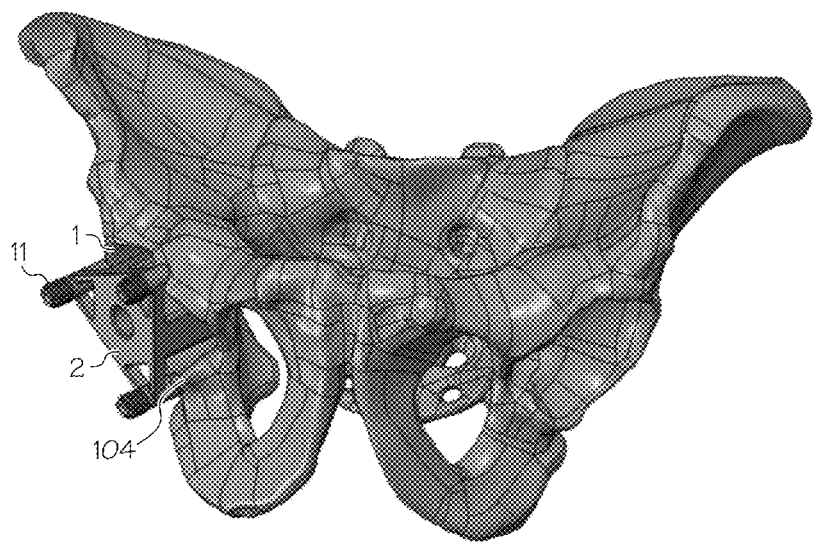
Figure 5A:
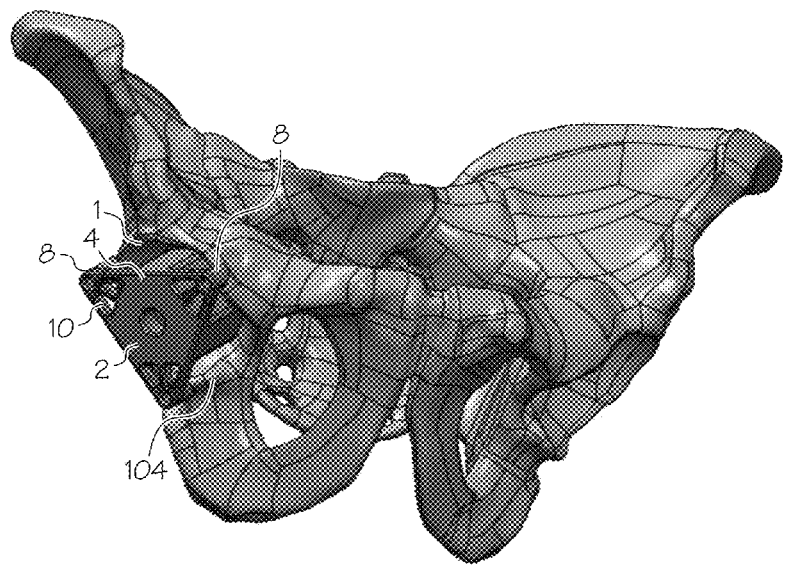
FIG. 5A illustrates an exemplary pin-locating jig positioned in the acetabulum prior to insertion of surgical pins. 5B illustrates an exemplary pin-locating jig after insertion of surgical pins prior to clipping of tabs to remove the body.
Figure 5B:
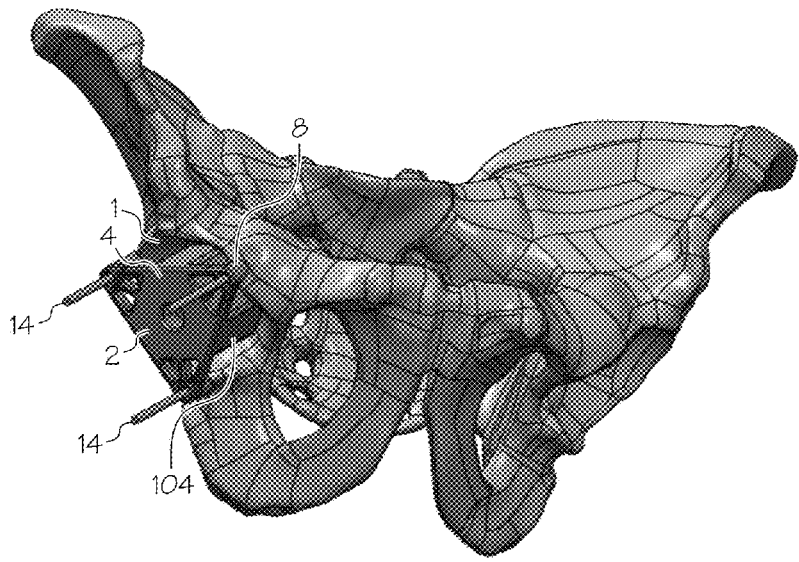

An acetabular reaming and impacting assembly is generally designed to control the angle of acetabular cup reaming and impacting during a THA procedure, and to provide adjustable control over the depth of reaming. A patient-specific acetabular reaming and impacting assembly according to embodiments of the invention comprises jigs manufactured from the patient-specific model, and jigs integrated with proprietary tool devices. Referring to FIGS. 3, 4 and 5, according to one embodiment, the assembly comprises a pin locating jig 2 comprising a body 4 having a periphery 6 and a least three patient-specific cannulated nubs 8, each nub attached to the periphery 6 by at least one tab 10 and having at least one end 12 contoured to engage a portion of an outer rim 104 of an acetabulum 1 of the patient at a self-selecting position and through which a surgical pin 14 may be inserted and secured to the outer rim 104 of the acetabulum 1. The pin locating jig 2 may be manufactured to achieve patient-specificity by the contoured ends 12 of the nubs 8, which match a portion of the patient's acetabulum rim topography, and in some embodiments the body 4 may further comprise at least one surface 40 contoured as a negative of an inner surface 5 of the patient's acetabulum 1. Where included, the additional contoured surface enhances the self-selective positioning of the jig on the acetabulum 1.

Figure 6:
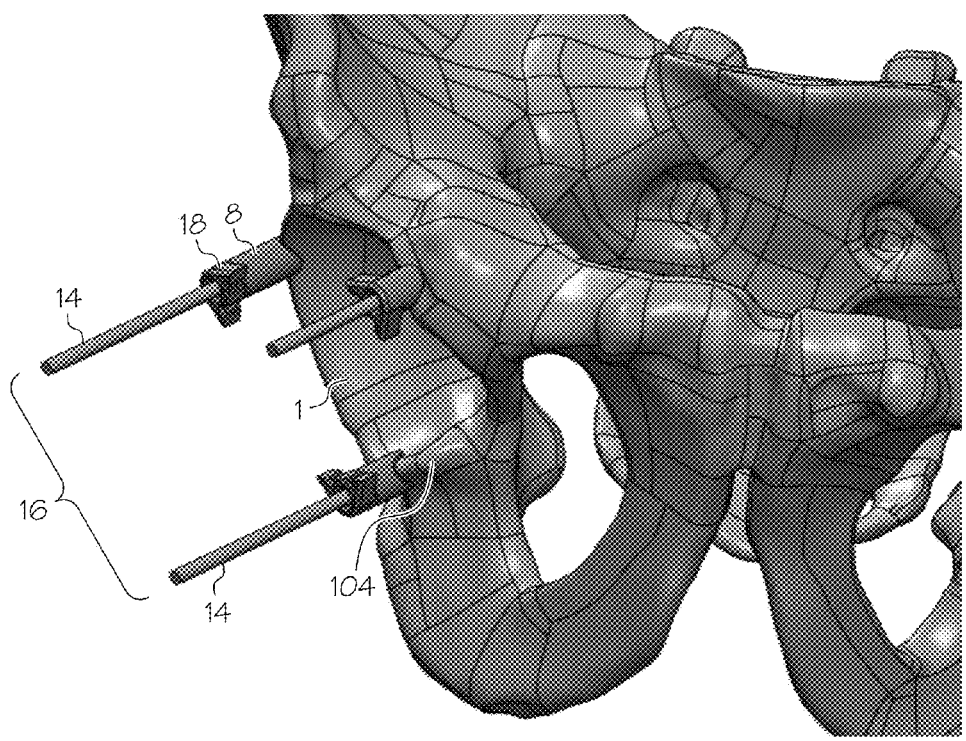
FIG. 6 illustrates a specific embodiment of a secured pin rail system formed after tabs are clipped from the pin locating jig.
Figure 7A:
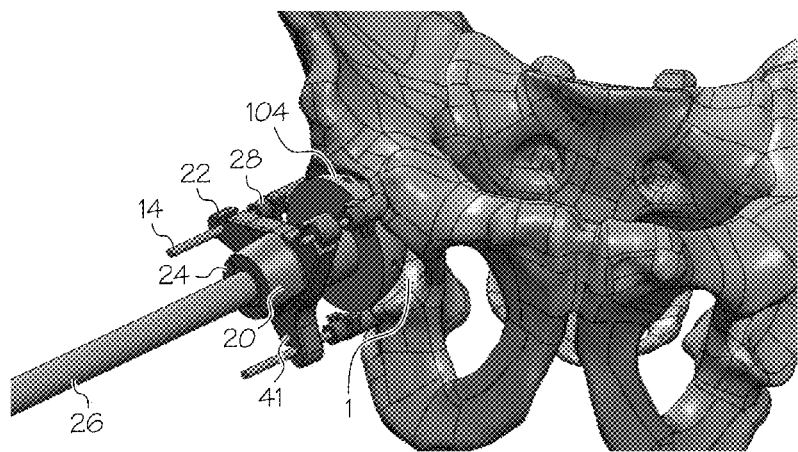
FIG. 7A illustrates an acetabular reamer engaged in an exemplary reamer jig being guided into position in the acetabulum by a pin rail system with spacer elements. 7B illustrates an acetabular reamer engaged in an exemplary reamer jig being guided into position in the acetabulum by a pin rail system with spacer elements comprising cannulated screw caps.
Figure 7B:
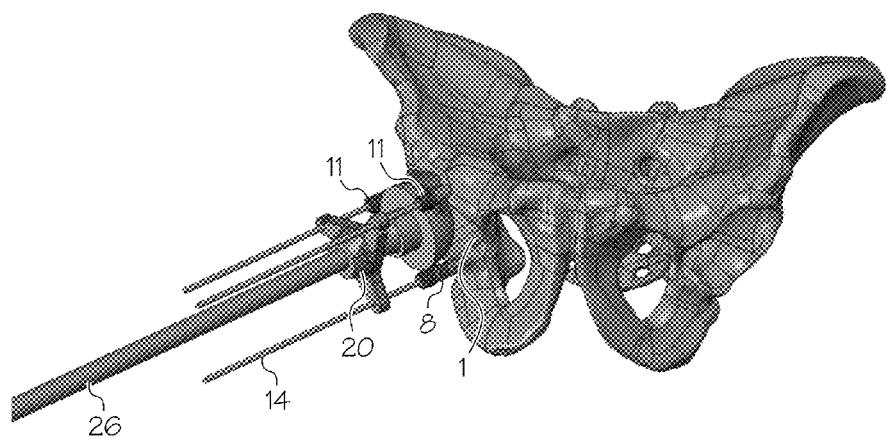

With reference to FIG. 6, upon removal of the body 4, a pin rail system 16 is formed. The pin rail system comprises at least three surgical pins 14, each secured through a nub 8 to the outer rim 104 of the acetabulum 1 forming a base 18. Removal of the body may be effectuated by clipping the at least one tab 10. According to some embodiments each nub 8 is attached to the body 4 by 1, 2 or 3 clippable tabs 10. Once the pin locating jig 2 is secured, the surgeon clips the tabs and discards the body 4 leaving the pin rail system 16 secured in place along the outer rim 3 of the acetabulum 1.

According to some embodiments, the assembly further comprises a removable reamer jig 20 comprising at least three peripheral pin holes 22, each hole corresponding to a pin 14 of the pin rail system 16 permitting engagement of the reamer jig 20 to the pin rail system 16, and an axial bore 24 through which an acetabular reaming device 26 may be inserted and attached. "Periphery" in the context of the reamer and impactor jigs according to the invention indicates a location at or near an outer edge of a geometric plane formed by the at least three pin holes and corresponding to an acetabular plane. The jig itself need not possess a planar morphology and may have various surface features and device attachment accommodations. According to specific embodiments each of the at least three peripheral pin holes 22 is located at the periphery by a spoke 41 extending from a perimeter of the axial bore. The spokes 41 may not be contiguous, may be partially contiguous, or may be substantially contiguous. In some embodiments of the reamer jig 20, the peripheral pin holes 22 are closed or substantially closed, and the jig 20 engages and disengages from the pin rail system 16 by sliding on and off the pins 14. In other embodiments of the reamer jig 20, the peripheral pin holes 22 are open and the opening is angled toward the periphery such that engagement and disengagement of the jig 20 to the pins 14 of the pin rail system 16 is effectuated by aligning the jig 20 in the pin rail system 16 and turning it clockwise or counter-clockwise, alternately with respect to engaging and disengaging.

The assembly may also comprise a set of spacing elements 28, generally one for each nub 8. The number of size of spacing elements may vary with the CAD generated for the patient. A spacing element may provide a discrete spacing accommodation, or a continuous spacing accommodation. The spacing element determines the depth to which the reaming device 26 will insert into the acetabular cup 102. In certain embodiments, a discrete spacing element may slide over a surgical pin 14 and sit at the base of the pin rail system 16. In other specific embodiments as depicted in FIGS. 3C and 3D and detailed in FIG. 4, a nub 8 may comprise a threaded portion 9 comprising a length and a pitch of threading, and a spacing element may be a cannulated screw cap 11 which screws onto the threaded portion 9 by an adjustable amount, providing a highly precise continuous spacing accommodation across the threaded portion 9.

Figure 8A:
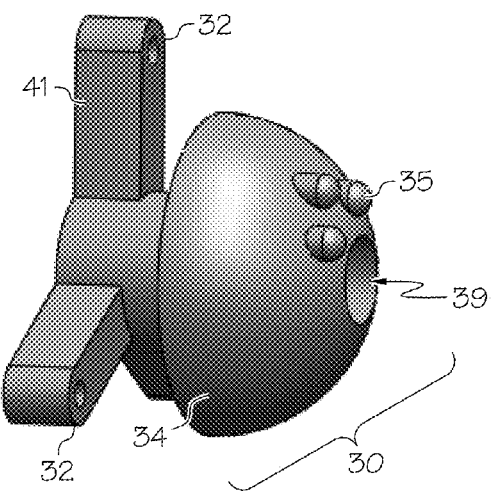
FIG. 8A depicts one embodiment of an impactor jig; 8B shows engagement of an impactor device through the axial bore of the impactor jig.
Figure 8B:
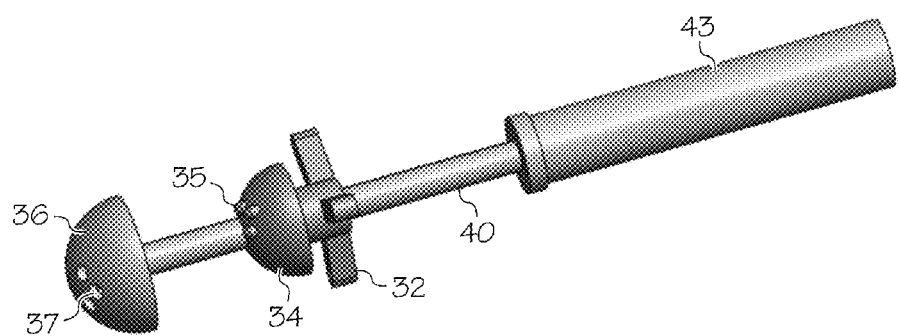
Figure 9A:
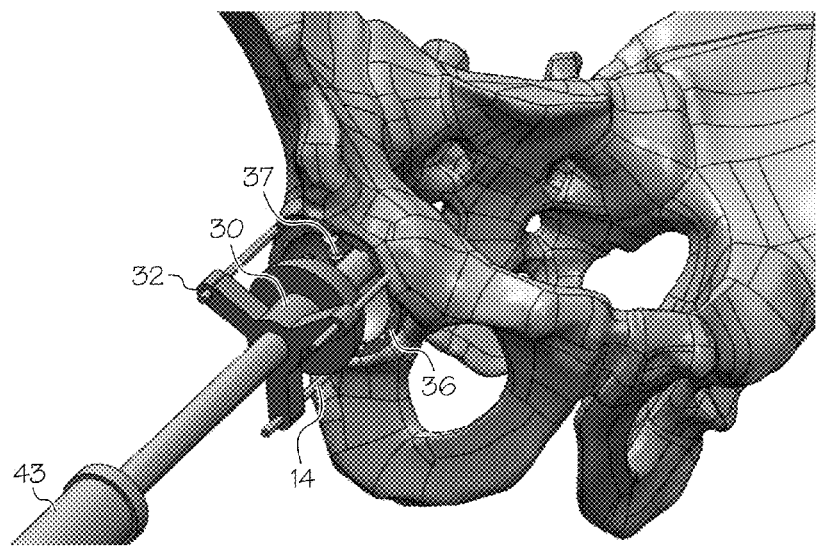
FIG. 9A shows engagement of an embodiment of an impactor jig to a pin rail system to guide the impactor cup into the acetabulum; 9B shows full insertion of the impactor jig into the impactor cup.
Figure 9B:
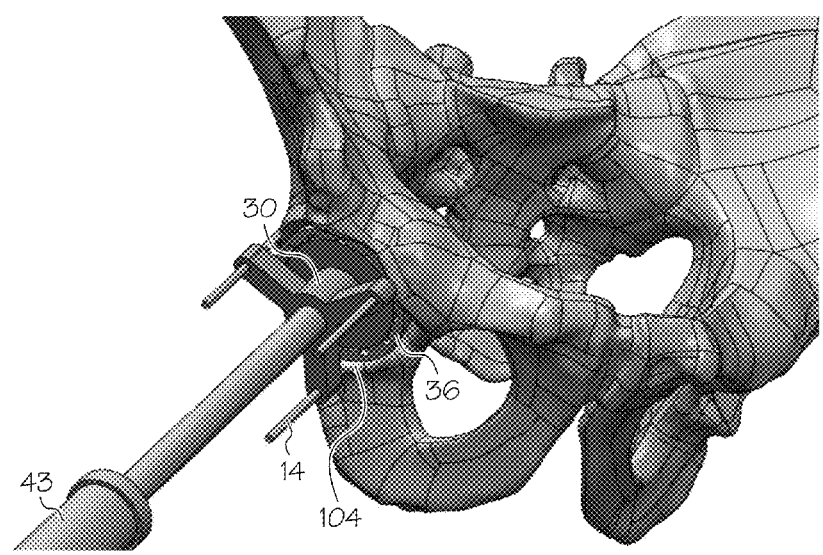
Figure 10A:
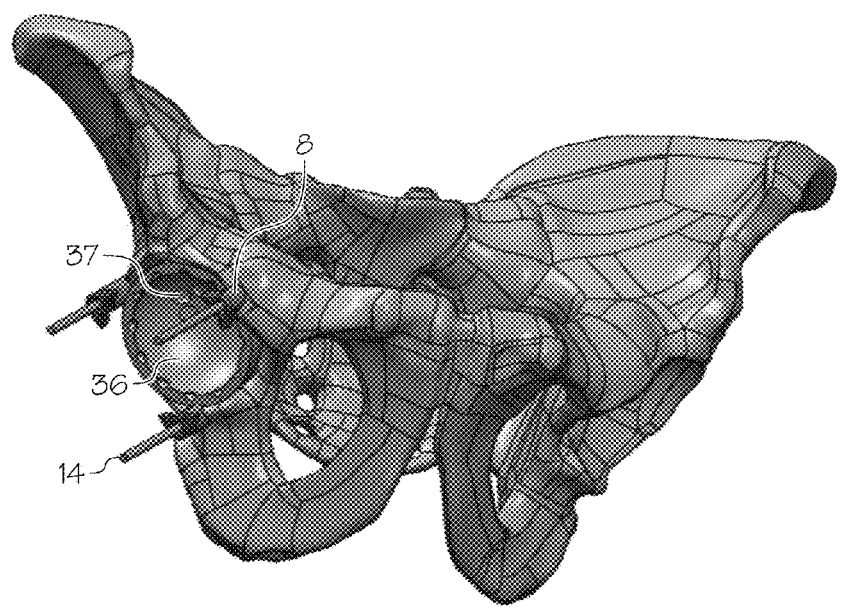
FIG. 10A shows an implant cup seated in the acetabulum with an exemplary pin rail system still secured; 10B shows the implant cup seated in the acetabulum after removal of the exemplary pin rail system.
Figure 10B:
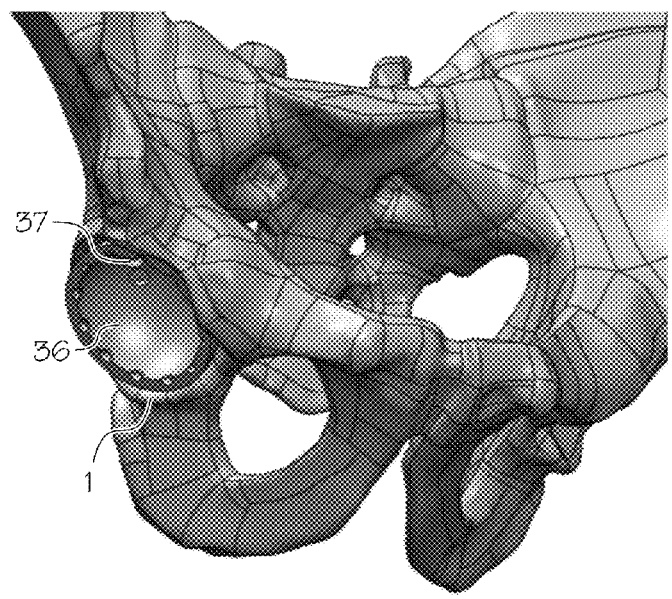

With reference to FIGS. 8, 9 and 10, the assembly further comprises a removable impactor jig 30 comprising at least three peripheral pin holes 32, each hole being substantially closed and corresponding to a pin of the pin rail system 16 such that the impactor jig 30 slidingly engages with and disengages from the pin rail system 16, and a cup portion 34 sized to fit into a prosthetic implant cup 36, and an axial bore 39 through which an acetabular impacting device 40 may be inserted to guide and impact the implant 36 into position in the acetabulum 1. The cup portion comprises an outer surface, the outer surface intended to operationally contact an inner surface of an implant cup. In specific embodiment the outer surface 33 of the cup portion 34 comprises a set of protrusions 35 located to fit and engage a corresponding set of screw holes 37 in the implant cup 36. According to specific embodiments, the desired location of the screw holes 37 is pre-operatively determined and patient-specifically modeled as protrusions 35 on the impactor jig 30. In some embodiments, the impacting device 35 comprises a handle 43 which slides and spins freely within the axial bore 39 of the impacting jig 30 such that when the jig cup portion 34 is inserted into the acetabular implant cup 36, the handle 43 may be turned, turning the implant 36 until the set of screw holes 37 in the implant cup 36 engages with the set of protrusions 35 on the impactor jig 30, which is held stationary by engagement with the pin rail system 16. The engagement of the protrusions 35 by the screw holes 37 restricts rotation of the implant cup 36 to a pre-operatively determined patient-specific angle.

Figure 11A:
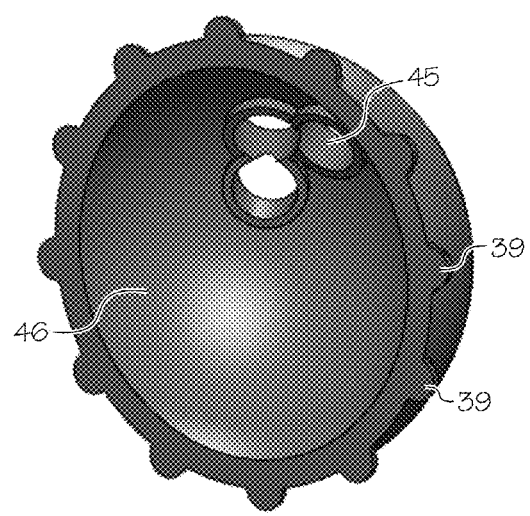
FIG. 11A illustrates a specific embodiment of an implant cup screw jig; 11B shows the screw jig inserted into the implant cup such that the screw jig holes align with the screw holes in the cup.
Figure 11B:
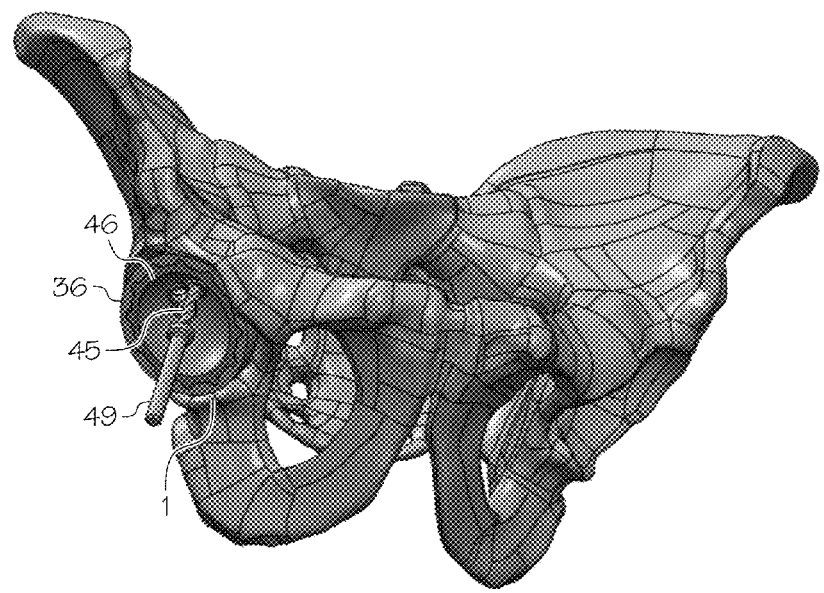

In certain embodiments, as specifically illustrated in FIG. 11, a plastic implant liner 46 is provided with a set of holes 45 which are designed to guide patient-specific placement of surgical screws 49 to secure the implant cup 36 and liner 46 into the acetabulum 1. The liner screw holes 45 correspond to the implant cup screw holes 37 and may be angled to guide insertion and drilling of the surgical screws 49. The implant liner 46 may also include one or more corrugations 39 forming a corrugated pattern along an outside peripheral edge of the liner 46 which matches and engages a corresponding corrugated pattern along an inside peripheral edge of the implant liner 46 thereby securing it into proper position within the implant cup 36.

Aspects of the acetabular reaming and impacting assembly, including features of the pin locating jig, spacer elements, impactor jig, impactor jig cup portion, and screw locator jig are designed to be patient-specific matches to unique anatomical features of the particular patient by manufacturing according to a model generated pre-operatively by computer-aided design, from data derived by imaging of a pelvic acetabular region of the particular patient.

Figure 12A:
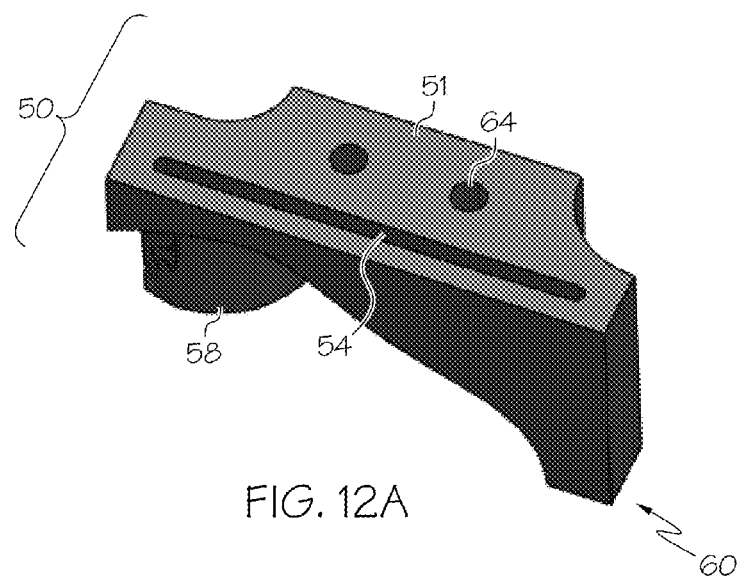
FIG. 12A depicts a specific embodiment of a patient-specific femoral resection jig; 12B illustrates placement of the jig on the femur and relative positioning of the surgical pin holes and cut guide.
Figure 12B:
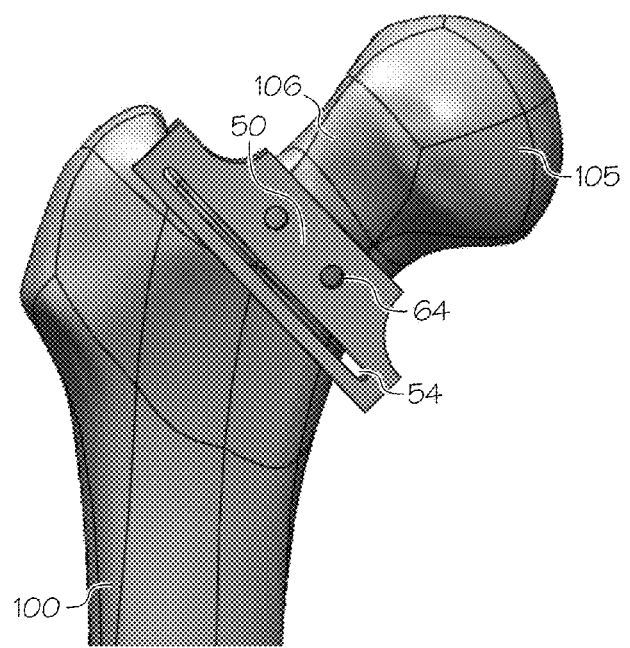

Another embodiment of the invention is directed to a patient-specific femoral resection jig 50. A specific embodiment is depicted in FIG. 12, with an alternative embodiment depicted in FIG. 15. The femoral resection jig is manufactured from a patient-specific model generated pre-operatively by computer-aided design from data derived from imaging of femoral region of the patient. The resection jig 50 comprises: a monolithic body 51 having at least proximal, distal, medial and lateral surfaces, the distal surface 52 providing a resection reference 54 for guiding a cutting instrument to resect a femoral head 105, the medial surface 56 comprising a patient-specific surface 58 contoured as a negative to a surface of the patient's femoral neck 106 such that the jig self-selects to engage a position on the surface of the femoral neck 106, and a medial-distal corner 60 positioned upon engagement to provide a visual indicator of version.

Figure 15A:
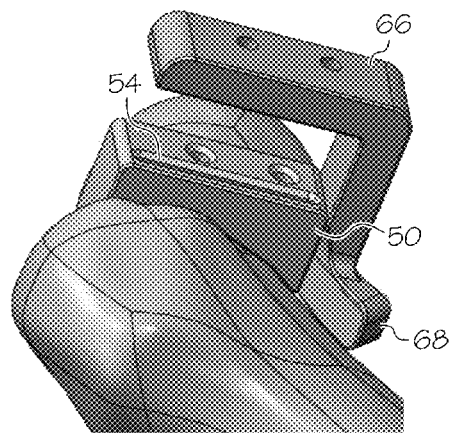
FIG. 15A depicts and exemplary embodiment of a femoral resection jig with a removable indicator; 15B illustrates the resection jig and indicator positioned together on the femur; 15C illustrates the resection jig in position after removal of the version indicator.
Figure 15B:
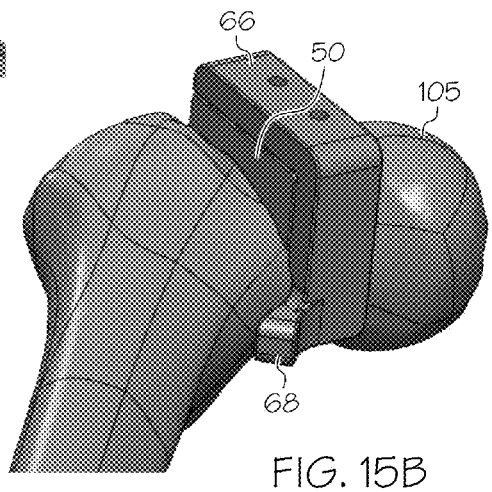
Figure 15C:
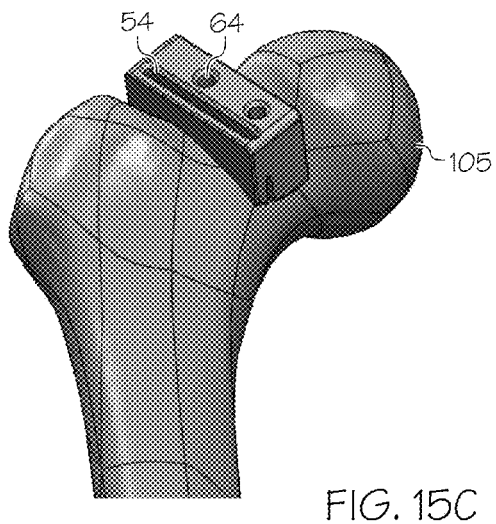

According to specific embodiments, the resection reference 54 may be a cut-guiding surface against which a surgical blade is placed and guided. In other specific embodiments the resection reference 54 is a slot in the monolithic body 51 in which a surgical blade may be placed and guided along the femoral neck 106. The resection reference 54 guides the blade both with respect to placement and angle. The monolithic body 51 may be any shape, so long as it provides the required faces. By "monolithic" it is understood that the body exists as a single operational unit, although the body may be manufactured in parts. In specific embodiments, the monolithic body is substantially in the form of a rectangular or trapezoidal prism. A femoral resection jig 50 will typically have holes 64 through which surgical pins may be inserted and drilled to secure the jig 50 to the femur 100. In a specific embodiment, the femoral resection jig has two surgical pin holes. In an alternative design, a femoral resection jig 50 comprises a removable version indicating guide 66, as depicted in FIG. 15. The version indicating guide 66 is patient-specific and located at a medial-distal corner 68 of the version indicating guide 66.

Figure 14:
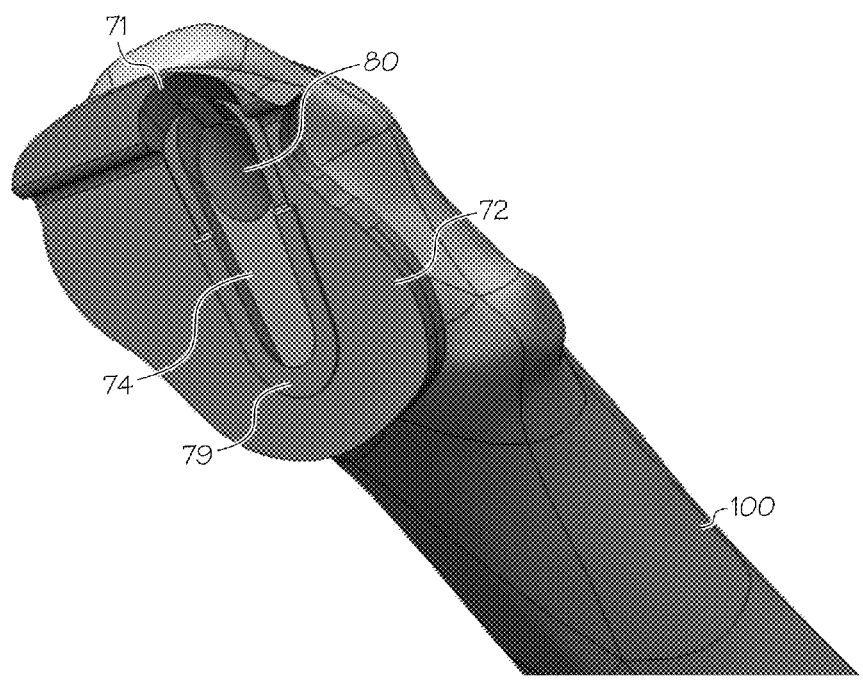
FIG. 14 illustrates a specific embodiment of a patient-specific femoral version guide having a broaching jig inserted into the opening of the femoral version guide.

Referring now to FIG. 13 and FIG. 14, an exemplary embodiment of a patient-specific femoral version assembly 70 is depicted. The femoral version assembly comprises a version guide 72 contoured to fit a portion of a rim 71 of a resected face 74 of a femur 100 and to substantially cover the resected face 74; the guide comprising an opening 75 to the resected face into which one or more standard insert jigs may be placed. Insert jigs may include a reaming jig 77, and a broaching/implant placement jig 78. The insert jigs may be seated and removed under intra-operational conditions. A specific jig insert comprises a reaming jig insert 77 comprising an opening positioned to direct a reamer through the resected face of the femur, guiding the reamer down the intramedullary canal 80. Another specific jig insert comprises a broaching jig insert 78 comprising an opening positioned to direct a broach into the resected face of the femur with the correct anteversion. A suitable broaching jig may also be an implant placement jig, or the implant placement jig may be a distinct insert.

A patient-specific femoral version assembly comprises a version guide manufactured from a patient-specific model generated pre-operatively by computer-aided design from data derived from imaging a contemplated resected femoral face and rim of the contemplated resected femoral face of the patient. Femoral version guides all have the same shape and size cut-out, with a set position for the insert jigs. A set of reamer insert jigs, one for each size of a reamer is provided, allowing for serial reaming. The reamer insert jigs are all shaped to fit the cut-out; however the opening may be serially adapted. Standard femoral broach insert jigs are also sized to fit the version guide cut-out. Broaching insert jigs comprise an opening shaped exactly to a cross section of a broach. A set of broach insert jigs, one for each size broach, is provided, allowing for serial broaching. Standard femoral implant insert jigs all have the same shape and size perimeter designed to fit the version guide cut-out. The implant insert jig comprises an opening shaped exactly to the cross section of the femoral stem implant. A set of implant jig inserts, one for each size femoral stem implant, is provided, allowing for the implantation of the appropriately sized implant. In particular embodiments a broach insert jig may function as an implant insert jig.

Additional embodiments of the invention are directed to methods. According to one embodiment, a method for fabricating a patient-specific acetabular reaming and impacting assembly comprises generating a computer-aided design-based model of a pelvic acetabular region of a patient. The model comprises a referencing coordinate system generated from 3-D imaging of the patient's relevant anatomy, in particular the pelvic acetabular regions with respect to THA. Features of a jig in accordance with the invention may be designed to precisely fit the surface topography of the patient's bone and therefore, when guided generally into place by the surgeon, self-selectively engage with the matching portion of the pelvic acetabular region. Spacer dimension and number may also be determined in accordance with the model to reflect and accommodate desirable depth and angle of insertion of the prosthetics. Jig features may be designed to provide more precise placement and angulation of surgical pins, tools and screws, and to provide precise guidance as to a desired resection location and plane.

Methods for fabricating a patient-specific femoral resection jig, for example, comprise generating a computer-aided design model of a head and neck region of a femur of a patient, superimposing a reference coordinate system on the anatomical structures based on the patient's specific anatomy, and constructing a model of a patient-specific femoral resection jig in accordance with the reference. It is understood that the surgeon ultimately selects securing/incision/resection points, aided by the anatomical models, and the surgeon's selection is incorporated into a jig model. In a specific example of patient specificity, a femoral version guide may be fabricated to precisely fit the resected face and rim of a patient's femur in order to provide the surgeon with an efficient guide to resection and broaching, as determined pre-operatively by the surgeon upon inspection of the computer aided design.

The instant inventive methods, devices and jigs integrate into a total hip arthroplasty system providing patient-specific control of hip geometry such that a femoral stem implant and an acetabular cup implant are positioned relative to one another with a hip geometry ideal for a specific patient. The total hip arthroplasty system includes design and fabrication of various embodiments of a patient-specific acetabular reaming and impacting assembly, a removable impactor jig, a patient-specific femoral resection jig, and a patient-specific femoral version assembly. The total hip arthroplasty system provides patient-specific accommodation of, for example, anteversion, vertical tilt, acetabular reaming depth, femoral reaming, location and angle of femoral broaching, and location and angle of femoral stem implantation.

It is understood however, that depending on the condition and indications of a particular patient, aspects and embodiments of the total hip arthroplasty system may be utilized independently of one another. For example, a patient-specific femoral resection jig and femoral version assembly may be utilized in a hemiarthroplasty procedure.

EXAMPLES

The following examples are intended to illustrate specific embodiments, aspects and features and should not be construed to limit the full scope of the claims as set forth herein.

Example 1

This Example illustrates a particular cadaveric protocol for pre-operative design aspects of a patient-specific total hip arthroplasty system.

Pre-operative CT-Scanning may be undertaken to provide information about a patient's anatomical geometry and bone structure, including for example bone surface topography. Reference points may be created or identified. For example, three surgical pins may be pre-operative inserted. The patient is CT-imaged in a normal supine position and in several alternative positions. Anywhere from 3 to 10 scans is acceptable, although more scans may be taken as time and resource commitment permits. At least one CT-image is taken with enough traction on the leg to pull the femoral head from the acetabular cup and the traction is recorded. The CT-scans are processed to generate anatomical planes and an anatomical plane coordinate system. In very specific exemplary embodiments, the CT-scans are processed using Amira™ software into .STL files for SolidWorks™ (Solid-Works is a proprietary software product for 3-D modeling in a wide variety of industries and is licensed from Dassault Systèmes SolidWorks Corp. of Waltham, Mass.). The .STL files are imported into SolidWorks™ to generate anatomical planes (sagittal, coronal, lateral, e.g., in accordance with ordinary meaning) and the distance of each plane to each surgical pin is measured. Software may be employed to create a template of the hip from this data. In a specific embodiment, DePuy proprietary software (DePuy Companies is a part of the Johnson & Johnson Companies and the licensor of Pinnacle® hip system and Summit® cementless hip system tools and corresponding software) may be utilized in conjunction with imaging data to determine appropriate implant size and approximate location for right and/or left hip replacements. Specific prosthetics/implants are selected and modeled in SolidWorks™ to create a model assembly. In a specific embodiment, a Summit™ femoral implant and a Pinnacle® acetabular cup implant are modeled and placed in approximate implantation location. Positioning of the implants is confirmed or adjusted by a surgeon checking against the template generated from the DePuy hip templating software. A suitable location for femoral resection and acetabular cup placement is determined in Solid-Works™ for the affected hip joint. Screen shots are taken of the templating assembly showing the final location of the implants. It is understood that a surgeon determines final locations of resection and implant positions with reliance on the modeling for precise guidance.

Figure 2A:
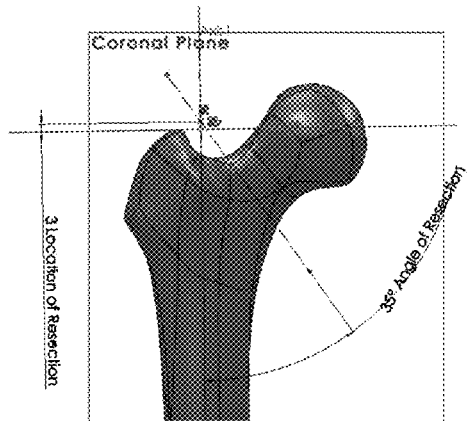
FIG. 2A illustrates determination of the distance from the origin to an intersection of femoral plane and femoral axis and shows the angle of the femoral resection plane with respect to the sagittal plane and coronal plane; 2B shows a secondary angle of resection; 2C Shows the vertical tilt of the acetabular cup plane, measured from the sagittal plane, and the method of determining the location of the cup plane; 2D Shows the anteversion of the acetabular cup plane (90-75=Anteversion), measured from the coronal plane.
Figure 2B:
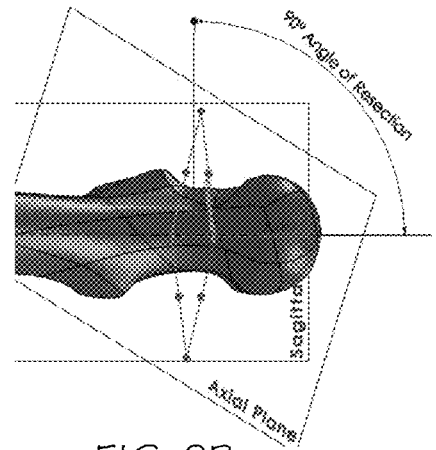

The position of a femoral resection plane and acetabular cup location with respect to the anatomical plane coordinate system is recorded. The angle of the femoral resection plane with respect to the sagittal plane and coronal plane is recorded and the distance from the origin to an intersection of femoral plane and femoral axis is determined as shown in FIG. 2A. A secondary angle of resection is illustrated in FIG. 2B.

Figure 2C:
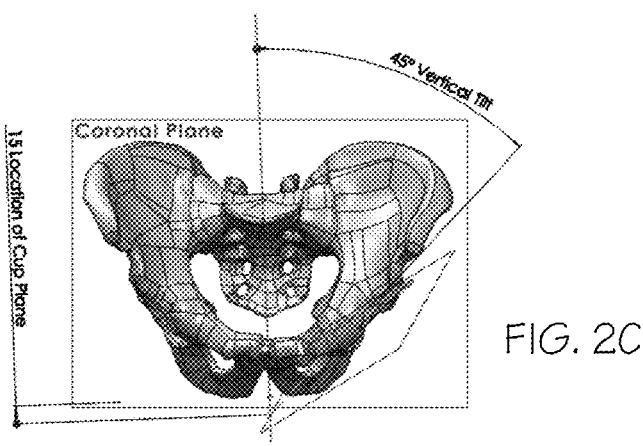
Figure 2D:
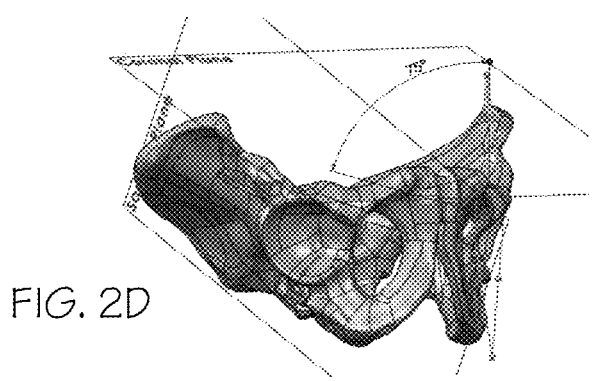

The angle of anteversion and vertical tilt of the acetabular cup plane are shown in FIGS. 2C and 2D. FIG. 2C illustrates the distance from origin to intersection of acetabular cup plane and longitudinal axis. The distance from the center of the cup on acetabular plane to the opposing, internal/proximal face of hip bone is shown in FIG. 2D.

The following provides a basic algorithm for the creation of the relevant anatomical planes.
1. Pelvis
  a. Create the Sagittal plane using a mid-point on the pubis, the most inferior point on the sacrum, and a midpoint on a lumbar spine.
  b. Create the Coronal plane by selecting the anterior most point on the iliac spine, the anterior most point on the pubis, and setting the plane perpendicular to the Sagittal plane.
  c. Create the Axial plane by selecting the inferior most point on the ischium and setting the plane perpendicular to the Sagittal plane and Coronal Plane. The intersection of these three planes is now to be considered the origin.
  d. Create the Acetabular Cup Plane
    1. Set the anteversion by drawing a line on the Coronal plane superiorly from the origin with the angle measured from the Sagittal plane.
    2. Set the vertical tilt by drawing a line on the Axial plane posteriorly from the origin with the angle measured from the Sagittal plane.
    3. A plane is created from the two lines defined in the two previous steps. This plane specifies the angle of the cup.
2. Femur
  A. Generate femoral axis
    a. Create a plane 15 mm±1 mm inferior to the lesser trochanter as close to perpendicular with the femur as possible.
    b. Find the center of the intramedullary canal on the new created plane by finding the intersection of two diameters (one of which is coincident on the Linea Aspera).
    c. Create a second plane parallel to the one created in 2(A)(a) 60 mm±1 mm superior to the epicondyles.
    d. Find the center of the intramedullary canal on this new created plane by drawing a sagittal line through the cross-section and finding the midpoint.
    e. The femoral axis is created by selecting the two created points within the intramedullary canal.
    f. Generate the axial plane by setting the plane perpendicular to the femoral axis and coincident to the superior-most point on the greater trochanter.
  B. Generate the Coronal Plane
    a. On the Axial plane, draw the transepicondylar axis by connecting the lateral and medial epicondylar peaks.
    b. The Coronal plane is generated by setting the plane perpendicular to the Axial plane, parallel with the line created in step 2(B)(a), and coincident with the femoral axis created in step 2(A)(e).
  C. Generate the Sagittal plane
    a. set the plane perpendicular to the Coronal plane and coincident with the femoral axis.

The above process allows a set of DICOM images to be changed into a SolidWorks™ surface, from which an anatomical coordinate system can be defined. This process can be validated and optimized by changing the values for threshold, number of faces, max dist, and min dist.

Example 2

This example illustrates an aspect of data transfer of the CT-scan DICOM images into 3-D models in SolidWorks™ using Amira™ (Amira is a proprietary software platform for 3-D and 4-D data visualization, processing, and analysis in life science applications and is licensed from FEI Visualization Sciences Group, Bordeaux, France).

A CT scan takes a large number of 2-D x-rays and uses geometric processing to create a 3-D image. Each x-ray or slice creates a DICOM image. The combination of the 2-D x-ray resolution and the slice thickness creates a voxel (volumetric pixel). According to a very specific embodiment, the CT data used has a voxel size of 0.78125 mm×1.2 mm×0.78125 mm. Amira™ is a 3-D data visualization, analysis, and modeling program. In particular embodiments it may be employed to separate the desired anatomy from the rest of the CT scan data and convert the data into a format that can be imported into SolidWorks™ as a 3-D model. STL files are created. The STL files approximate the geometry of the data by simplifying it into a specified number of triangles. STL files are easily imported into SolidWorks™.

Example 3

This example illustrates methods and particular embodiments of the assemblies, jigs and systems according to the invention through an exemplary Total Hip Arthroplasty procedure on a cadaver.

STL mesh files of CT scans are processed into surfaces in SolidWorks™. The femoral resection guides in SolidWorks™ are updated to reflect patient-specific bone geometry and a surgeon approves the line of resection. Anterior and posterior jig systems may be created for both left and right femurs. The SolidWorks™ acetabular guide system is also updated to reflect patient-specific bone geometry and a surgeon approves the angle of anteversion, vertical tilt, and depth. One rim locating jig model and one cup locating jig model may be created for either or both of the left and right hip.

The THA procedure is performed on the right and left hip of the cadaver using the patient-specific reaming, resecting, and impaction jigs according to embodiments of the invention. An anterior approach is used on one side, while a posterior approach is used for the other. Upon completion of the procedure, the cadaver is transported to radiology for CT-imaging. This post-op imaging includes supine position scans. The scans are analyzed.

Data Analysis

Plane Generation. Anatomical planes are generated by defining the distances from the surgical pins to each plane defined in Example 2.

Acetabular Cup Location and Angulation Determination. The angle of the implanted acetabular cup is determined with respect to the anatomical planes for both the left and right hip. The angle of the cup placement is compared to the pre-operative intended angulation for both the left and right hip. The coordinates of the center of the cup on the plane of cup angulation is calculated with respect to the anatomical planes for both the left and right hip. Cup placement is compared to the pre-operative intended location for both the left and right hip. The distance from the center of the acetabular implant to the proximal face of the hip bone for both the left and right hip and compared to the pre-operative intended distance for both the left and right hip.

Femoral Plane Location and Angulation Determination. The angle of resection on the femoral neck with respect to the anatomical planes are determined for both the left and right femur, and compared to the pre-operative intended angulation for both the left and right femur. The location of the intersection of the femoral resection plane and the femoral axis is determined for both the left and right femur, and compared with the pre-operative intended location for both the left and right femur.

Criteria for Success

Acetabular Reaming and Impacting Assembly
1. Pin location jig fits onto Acetabular cup securely
2. Pins can be placed using pin location jig
3. Pin location jig can be clipped leaving behind only the spacer pieces on bases
4. Reamer jig connects DePuy Acetabular reamer to pins and allows for Acetabular reaming
5. Spacers function to restrict acetabular reaming to a specified depth
6. Impactor jig connects DePuy Acetabular cup impactor to pins and allows for Acetabular implant impacting
7. Entire Acetabular reaming and impacting assembly can be removed from surgical field
8. Acetabular cup is anteverted within +/−10° of desired angle (range of safe zone in the art)
9. Acetabular cup has a vertical tilt within +/−10° of desired angle (range of safe zone in the art)

Femoral Resection and Version Assembly
1. Femoral resection jig fits onto the neck of the femur securely
2. Femoral resection jig can be securely fixed to femoral neck
3. Version indicator can be made and seen during broaching and stem impaction
4. Neck cut can be made along the femoral cutting reference
5. Neck cut is in target location
6. Midplane of stem aligns with the target location Clinical Outcome
1. Leg is adjusted to appropriate length
2. Hip is adjusted to appropriate offset Example 4

This Example illustrates a THA procedure illustrating specific embodiments of methods, an acetabular reaming and impacting assembly and a femoral resection and version assembly in accordance with the invention.

An acetabular reaming and impacting assembly includes the major components of a pin location jig, a pin rail system, an acetabular reaming jig, an acetabular impacting jig, and optionally a screw locating jig. The jigs are patient-specifically designed to control the angle of acetabular cup reaming and impacting during a THA procedure. The assembly, and in particular the pin rail system and spacers, also controls the depth of reaming. The hip joint is exposed and the femur is dislocated from the Acetabular cup as in normal THA procedure. The rim of the cup is cleaned such that the bone contouring pin locator can be placed onto the cup. The pin locating jig is placed on the Acetabular cup. The cup should self-select a position . . . that is, it assumes a distinct position in which it sits and feels secure. Surgical pins are drilled into position using the pin locator. The tabs located at each nub are clipped. The nubs are left to set a base plane for the spacers and the body of the pin locator is removed. Spacers are stacked on each pin to a desired height. In alternative embodiments a spacer element comprising a cannulated screw cap is screwed onto a threaded portion of a nub a predetermined height. The desired height is determined to control the depth of the reamer. The reamer guide is attached to, for example, a DePuy hip system Reamer. The reamer is moved into the surgical field and the reamer jig is rotated until it engages with the 3 pins of the pin rail system. Reaming is performed to the depth allowed by the spacers. Spacer height may be adjusted intraoperatively until the desired reaming depth has been achieved. Afterward, the reamer and reamer jig are removed from the surgical field. The impactor jig is then attached to the DePuy hip system Impactor. The impactor is moved into surgical field and impactor jig may be engaged to the pin rails by sliding from the top through the pin holes in the jig, or in alternative embodiments it may be rotated until it engages with the rails of the pin rail system. The acetabular cup is impacted into position and thereafter the impactor and impactor jig are removed from the surgical field. The surgical pins are then removed from the pelvis. The femur is re-approximated to the cup and wound is closed as in a normal THA procedure.

The femoral jig is designed to control and guide the location and angle of the femoral neck cut during a THA procedure. In some embodiments the inventive jig also allows for the creation of a visual indicator of version to assist in alignment during broaching and stem impaction. In some embodiments the resection jig and version jig are an inseparable single body. In other specific embodiments the resection jig and version jig are two distinct pieces. The femoral resection jig is patient-specifically designed to fit in position on the femoral neck in a self-selecting location. The resection jig may include pin holes so that it may be attached to the neck of the femur using surgical pins. The resection jig may have a reference cutting face which permits location of the precise femoral neck cut and guiding of the femoral resection tool. In some embodiments the resection jig may comprise a slot which operates to guide the resection tool. The jig may also have a corner by which a mark can be made on the bone to indicate proper version.

The hip joint is exposed and the femur is dislocated from the acetabular cup as in an ordinary THA procedure. In a very specific embodiment, the femoral resection jig is placed onto the neck of the femur and should self-locate into a distinct position in which the jig will feel secure. The jig may be specifically designed for placement on either the anterior or posterior side of the neck and the side chosen will depend on the type of approach being performed. Surgical pins are drilled into position to fix the resection jig in place. A linear mark may be made on the femur adjacent to the most medial and distal corner of the guide. This mark indicates proper version for the femoral implant. A femoral neck cut is made using a surgical cutting tool such as a surgical saw, thus resecting the femoral head. Care is taken to keep the blade flat against the resection jig reference cutting face in order to avoid cutting at an oblique angle. The intramedullary canal is broached and the femoral stem implant is impacted in accordance with ordinary THA procedures; however using the bone mark as a visual indicator of proper version. In other specific embodiments a femoral version jig may be positioned across the face of the femur to be broached. The jig is patient-specifically designed to self-select a position on the rim of the resected femur and to provide a guide for insertion of broaching devices. The femoral version jig includes a cut-out for insertion of broaching jigs which guide the broaching procedure. As before, the femoral stem implant is impacted in accordance with ordinary THA procedures. The femur is then reapproximated to the cup and the wound is closed.

What is claimed:

1. A patient-specific acetabular reaming and impacting assembly comprising:
   a pin locating jig comprising a body having a periphery and a least three patient-specific cannulated nubs, each nub attached to the periphery by at least one tab and having at least one surface contoured to engage a portion of an outer rim of an acetabulum of the patient at a self-selecting position and through which a surgical pin may be inserted and secured to the outer rim of the acetabulum, where upon removal of the body a pin rail system is formed comprising at least three surgical pins, each secured through a nub forming a base;
   a removable reamer jig comprising at least three peripheral pin holes, each hole corresponding to a pin of the pin rail system permitting engagement of the reamer jig to the pin rail system, and an axial bore through which an acetabular reaming device may be inserted and attached;
   at least one set of spacing elements;
   a removable impactor jig comprising at least three peripheral pin holes, each hole corresponding to a pin of the pin rail system permitting sliding engagement of the impactor jig to the pin rail system, and a cup portion sized to fit into an implant cup, and an axial bore through which an acetabular impacting device may be inserted to guide and impact the implant into position in the acetabulum.

2. The acetabular reaming and impacting assembly according to claim 1, wherein removal of the locating jig body is achieved by clipping the tabs.

3. The acetabular reaming and impacting assembly according to claim 1, wherein the body of the locating jig comprises at least one patient specific surface contoured as a negative of an inner surface of the acetabulum to enhance self-selection positioning of the jig on the acetabulum.

4. The acetabular reaming and impacting assembly according to claim 1, wherein the spacing elements are spacers for placement at the base of each pin of the pin rail system to provide patient-specific control of the depth of the reamer device.

5. The acetabular reaming and impacting assembly according to claim 1, wherein the nubs comprise a threaded portion and each spacer element comprises a cannulated screw cap which screws to a nub to an adjustable height to provide patient-specific control of the depth of the reamer device.

6. The acetabular reaming and impacting assembly according to claim 1, wherein the at least three peripheral pin holes of the reamer jig are open and oriented such that the reamer jig may be engaged or disengaged from the pin rail system by turning the reaming device clockwise or counterclockwise.

7. The acetabular reaming and impacting assembly according to claim 1, wherein the at least three peripheral pin holes of the impactor jig are open and oriented such that the impactor jig may be engaged or disengaged from the pin rail system by turning the impactor device clockwise or counterclockwise.

8. The acetabular reaming and impacting assembly according to claim 1, wherein the at least three peripheral pin holes of the impactor jig are closed such that the impactor jig may be engaged or disengaged from the rail system by sliding on and off the pin rail system.

9. The acetabular reaming and impacting assembly according to claim 1, wherein an outer surface of the cup portion of the impactor jig comprises a set of protrusions located to fit and engage a corresponding set of patient-specific screw holes in the implant cup.

10. The acetabular reaming and impacting assembly according to claim 9, wherein the impacting device comprises a handle which slides and spins freely within the axial bore of the impacting jig such that when the jig cup portion is inserted into the acetabular implant cup, the implant cup may be turned until the set of screw holes engages with the set of protrusions, restricting rotation of the implant cup to a patient-specific angle.

11. The acetabular reaming and impacting assembly according to claim 2, wherein the nubs of the locating jig are each attached to the periphery of the jig by a single tab.

12. The acetabular reaming and impacting assembly according to claim 1, wherein each pin hole at the periphery of the reaming jig and/or each pin hole at the periphery of the impacting jig are located at the periphery by a spoke.

13. The acetabular reaming and impacting assembly according to claim 1, wherein the implant cup comprises a set of screw holes and the assembly further comprises insertion of an implant liner comprising patient specific implant screw holes specifically positioned to guide insertion and drilling of one or more surgical screws to secure the implant cup and liner into the acetabulum; wherein the liner screw holes correspond to and engage the set of screw holes in the implant cup.

14. The acetabular reaming and impacting assembly according to claim 1, wherein the pin locating jig, spacer elements, and impactor jig cup portion protrusions are formed from a patient-specific model generated pre-operatively by computer-aided design from data derived from imaging of a pelvic acetabular region of the patient.

15. A patient-specific femoral resection jig comprising:
a monolithic body having at least proximal, distal, medial and lateral surfaces, the distal surface providing a resection reference for guiding a cutting instrument to resect a femoral head, the medial surface comprising a patient-specific surface contoured as a negative to a surface of the patient's femoral neck such that the jig self-selects to engage a position on the surface of the femoral neck, at least one hole through which surgical pins may be inserted to secure the jig to the femur, said at least one hole located on the jig such that when the jig is engaged, the surgical pins only insert into a portion of the femoral head to be resected, and a medial-distal corner positioned upon engagement to provide a visual indicator of version.

16. The femoral resection jig according to claim 15, wherein the resection reference comprises a cut-guiding surface.

17. The femoral resection jig according to claim 15, wherein the resection reference comprises a cut-guiding slot.

18. The femoral resection jig according to claim 15, wherein the monolithic body is substantially in the form of a rectangular or trapezoidal prism.

19. The femoral resection jig according to claim 15, further comprising at least two holes through which surgical pins may be inserted to secure the jig to the femur.

20. The femoral resection jig according to claim 15, formed from a patient-specific model generated pre-operatively by computer-aided design from data derived from imaging of femoral region of the patient.

21. A patient-specific femoral version assembly comprising:
a version guide contoured to fit a portion of a rim of a resected face of a femur and to substantially cover the resected face, the guide comprising an opening to the resected face into which a set of jig inserts including a standard reaming jig, a broaching jig and an implant placement jig may be seated and removed under operational conditions.

22. The patient-specific femoral version assembly according to claim 21, wherein the jig insert comprises a reaming jig comprising a hole positioned to direct a reamer through the resected face.

23. The patient-specific femoral version assembly according to claim 21, wherein the jig insert comprises a broaching jig comprising a hole positioned to direct a broach into the resected face.

24. The patient-specific femoral version assembly according to claim 21, wherein the jig insert comprises an implant placement jig comprising a hole positioned to direct an implant into the resected face.

25. The patient-specific femoral version assembly according to claim 21, wherein the version guide is formed from a patient-specific model generated pre-operatively by computer-aided design from data derived from imaging of a contemplated resected femoral face and rim of the contemplated resected femoral face of the patient.

26. A method for fabricating the patient-specific acetabular reaming and impacting assembly of claim 1, the method comprising: generating a computer-aided design model of a pelvic acetabular region of a patient, the model comprising a referencing coordinate system based on the patient's anatomy, and constructing a pin locating jig contoured to self-selectively engage with a portion of the pelvic acetabular region, and selecting spacer elements in accordance with the model.

27. The method according to claim 26, wherein the computer-aided design model is derived from 3-D images of the pelvic acetabular region.

28. The method according to claim 26, further comprising locating the set of protrusions on the outer surface of the cup portion of the impacting jig according to the model.

29. A method for fabricating the patient-specific femoral resection jig according to claim 15, the method comprising: generating a computer-aided design model of a head and neck region of a femur of a patient, the model comprising a referencing coordinate system based on the patient's anatomy, and constructing the femoral resection jig in accordance with the model.

30. The method for fabricating the patient-specific femoral version assembly according to claim 21 comprising: generating a computer-aided design model of a femur of a patient, the model comprising a referencing coordinate system based on the patient's anatomy, and constructing the femoral version guide in accordance with the model.

31. A total hip arthroplasty system providing patient-specific control of hip geometry such that a femoral stem implant and an acetabular cup implant are positioned relative to one another with a hip geometry ideal for the specific patient, the total hip arthroplasty system comprising:
(a) a patient-specific acetabular reaming and impacting assembly comprising:
a pin locating jig comprising a body having a periphery and a least three patient-specific cannulated nubs, each nub attached to the periphery by at least one tab and having at and at least one surface contoured to engage a portion of an outer rim of an acetabulum of the patient at a self-selecting position and through which a surgical pin may be inserted and secured to the outer rim of the acetabulum, where upon removal of the body a pin rail system is formed comprising at least three surgical pins, each secured through a nub forming a base;
a removable reamer jig comprising at least three peripheral pin holes, each hole corresponding to a pin of the pin rail system permitting engagement of the reamer jig to the pin rail system, and an axial bore through which an acetabular reaming device may be inserted and attached;
at least one set of spacing elements;
a removable impactor jig comprising at least three peripheral pin holes, each hole corresponding to a pin of the pin rail system permitting sliding engagement of the impactor jig to the pin rail system, and a cup portion sized to fit into an implant cup, and an axial bore through which an acetabular impacting device may be inserted to guide and impact the implant into position in the acetabulum;
(b) a patient-specific femoral resection jig comprising:
a monolithic body having at least proximal, distal, medial and lateral surfaces, the distal surface providing a resection reference for guiding a cutting instrument to resect a femoral head, the medial surface comprising a patient-specific surface contoured as a negative to a surface of the patient's femoral neck such that the jig self-selects to engage a position on the surface of the femoral neck, and a medial-distal corner positioned upon engagement to provide a visual indicator of version; and (c) a patient-specific femoral version assembly comprising:

a version guide contoured to fit a portion of a rim of a resected face of a femur and to substantially cover the resected face, the guide comprising an opening to the resected face into which a set of jig inserts including a standard reaming jig, a broaching jig and an implant placement jig may be seated and removed under operational conditions.

32. A method of performing a total hip arthroplastic procedure to provide patient-specific accommodation of anteversion, vertical tilt, acetabular reaming depth, femoral reaming, location and angle of femoral broaching, and location and angle of femoral stem implantation, the method comprising: employing the total hip arthroplasty system according to claim 31.

33. A hip hemiarthroplasty system providing patient-specific control of hip geometry such that a femoral stem implant is positioned relative to an acetabulum with a hip geometry ideal for the specific patient, the hip hemiarthroplasty system comprising:

(a) a patient-specific femoral resection jig comprising:
a monolithic body having at least proximal, distal, medial and lateral surfaces, the distal surface providing a resection reference for guiding a cutting instrument to resect a femoral head, the medial surface comprising a patient-specific surface contoured as a negative to a surface of the patient's femoral neck such that the jig self-selects to engage a position on the surface of the femoral neck, and a medial-distal corner positioned upon engagement to provide a visual indicator of version; and (b) a patient-specific femoral version assembly comprising:
a version guide contoured to fit a portion of a rim of a resected face of a femur and to substantially cover the resected face, the guide comprising an opening to the resected face into which a set of jig inserts including a standard reaming jig, a broaching jig and an implant placement jig may be seated and removed under operational conditions.

* * * * *